(12) United States Patent
Yoon et al.

(10) Patent No.: US 9,545,400 B2
(45) Date of Patent: Jan. 17, 2017

(54) ANALGESIC COMPOSITION INCLUDING OPIOID ANALGESIC AND P7C3

(71) Applicant: CHONNAM NATIONAL UNIVERSITY HOSPITAL, Gwangju (KR)

(72) Inventors: Myung Ha Yoon, Gwangju (KR); Sang Wan Ryu, Seoul (KR)

(73) Assignee: CHONNAM NATIONAL UNIVERSITY HOSPITAL, Gwangju (KR)

( * ) Notice: Subject to any disclaimer, the term of this patent is extended or adjusted under 35 U.S.C. 154(b) by 201 days.

(21) Appl. No.: 14/446,276

(22) Filed: Jul. 29, 2014

(65) Prior Publication Data

US 2015/0265595 A1    Sep. 24, 2015

(30) Foreign Application Priority Data

Mar. 18, 2014    (KR) ........................ 10-2014-0031869

(51) Int. Cl.

| | | |
|---|---|---|
| *A01N 43/42* | (2006.01) | |
| *A61K 31/44* | (2006.01) | |
| *A01N 43/40* | (2006.01) | |
| *C07D 471/00* | (2006.01) | |
| *C07D 491/00* | (2006.01) | |
| *C07D 401/00* | (2006.01) | |
| *A61K 31/485* | (2006.01) | |
| *A61K 31/403* | (2006.01) | |
| *A61K 31/00* | (2006.01) | |

(52) U.S. Cl.
CPC ............. *A61K 31/485* (2013.01); *A61K 31/00* (2013.01); *A61K 31/403* (2013.01)

(58) Field of Classification Search
CPC ........................... A61K 31/403; A61K 31/485
USPC ................. 514/282, 339; 546/87, 276.7
See application file for complete search history.

(56) References Cited

U.S. PATENT DOCUMENTS

| | | | | |
|---|---|---|---|---|
| 2006/0177381 | A1* | 8/2006 | Brooks-Korn | ....... A61K 31/135 424/10.1 |
| 2011/0003836 | A1* | 1/2011 | McKnight | ............ A61K 31/404 514/275 |
| 2012/0302590 | A1 | 11/2012 | Bhide et al. | |
| 2013/0184271 | A1 | 7/2013 | McKnight et al. | |
| 2013/0289061 | A1 | 10/2013 | Bhide et al. | |

OTHER PUBLICATIONS

Jesus-Cortes et al. (PNAS, 109, 42, 17010-17915.*
Panerai (J of Palliative care, 42-44, 1991).*

* cited by examiner

*Primary Examiner* — Uma Ramachandran

(57) ABSTRACT

Disclosed is an analgesic composition including an opioid analgesic and a therapeutically effective amount of P7C3, and the present analgesic composition may treat acute and facilitated pain very effectively, and has a significantly high synergistic effect compared to the effect by administration of individual drugs.

2 Claims, 6 Drawing Sheets

ANALGESIC COMPOSITION INCLUDING OPIOID ANALGESIC AND P7C3

CROSS-REFERENCE TO RELATED APPLICATIONS

This application claims priority to and the benefit of Korean Patent Application No. 10-2014-0031869 filed in the Korean Intellectual Property Office on Mar. 18, 2014, the entire contents of which are incorporated herein by reference.

TECHNICAL FIELD

The present invention relates to an analgesic composition including an opioid analgesic and P7C3, which are effective against tissue injury-induced acute pain and facilitated pain.

BACKGROUND ART

Tissue injuries after an operation and the like evoke pain. Tissue injury leading to chronic pain is a field in which medicinal treatment effects are not well satisfied. The exact mechanisms of chronic pain still remain to be determined.

A variety of neurotransmitters are known to be involved in nociceptive modulation in the central nervous system, and research activities have been focused on such neurotransmitters. However, no magic bullets have not been established.

Recently, aminopropyl carbazole (P7C3) was discovered, and systematic administration of P7C3 has shown neuroprotective effects in animal models of neurodegenerative disease without knowledge of the clear action mechanisms. However, analgesic effects of P7C3 against pain have not been known.

Opioid is an analgesic, which usually acts on the receptors located in the central nervous system, and morphine is a representative drug of opioid.

Morphine exhibits affinity for the $\delta$ and $\kappa$ opioid receptors, and is also active for the $\mu$ opioid receptors related to the central nervous system, brain, spinal cord, and thus exhibits effects such as pain alleviation, drowsiness, changes in mood, and mental clouding. Morphine belongs to a strong opioid class used for intermediate to severe pain. The opioids including morphine and morphine-like homologs have potent analgesic effects, but is reported to cause many side effects, for example, respiratory depression, nausea, vomiting, vertigo, clouding of consciousness, unpleasantness, pruritus, and constipation. Problems which aggravate biliary tract pressure, urinary tract retention, and hypotension symptoms have been reported. The development tolerance to opioid analgesia, the risks of drug dependency, the drug abuse, and the like are another undesirable effects. Therefore, studies on methods for decreasing the total amount of opioids used and obtaining synergistic effect for an analgesic action have continued.

SUMMARY OF THE INVENTION

The present invention has been made in an effort to provide an analgesic composition containing P7C3, which exhibits excellent analgesic effects against severe pain including acute pain and facilitated pain.

The present invention has also been made in an effort to provide an opioid-containing analgesic composition which may effectively treat a patient suffering from pain with opioid analgesics for a long period of time and simultaneously may reduce side effects, dependency and tolerance, which patients suffer from when taking opioids for a long period of time.

The present invention has also been made in an effort to provide an analgesic composition which may enhance analgesic effects of P7C3, and thus effectively treat the pain of a patient.

An exemplary embodiment of the present invention provides an analgesic composition for treating or alleviating tissue injury-induced acute pain and facilitated pain, including: an opioid analgesic or a pharmaceutically acceptable salt thereof; and a therapeutically effective amount of P7C3 or a pharmaceutically acceptable salt thereof.

According to an exemplary embodiment of the present invention, the opioid analgesic may be morphine.

According to another exemplary embodiment of the present invention, the opioid analgesic and P7C3 may be an analgesic composition included in a weight ratio of 8.8:31.8 or 3.9:31.

According to yet another exemplary embodiment of the present invention, the analgesic composition may be a formulation administered intrathecally.

Another exemplary embodiment of the present invention provides an analgesic composition for treating or alleviating tissue injury-induced acute pain and facilitated pain, including a therapeutically effective amount of P7C3 or a pharmaceutically acceptable salt thereof.

According to exemplary embodiments of the present invention, it is possible to treat acute and facilitated pain very effectively, and bring about significantly high synergistic effect compared to effects by means of individual drug administration for the analgesic composition of the present invention. Therefore, since the amount of opioid analgesics used may be reduced, side effects thereof may also be alleviated.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIGS. 1A and 1B illustrate the number of flinches over time in a formalin-induced pain test according to an exemplary embodiment of the present invention, in which FIG. 1A represents the number of flinches after the administration of P7C3 and FIG. 1B represents the number of flinches after the administration of morphine. All the measurement values are expressed as means±SEM of 6 to 7 rats.

FIG. 2A is the result of a Phase 1 response, and FIG. 2B is the result of a Phase 2 response. All the measurement values are expressed as means±SEM of 6 to 7 rats.

Figure 1A:
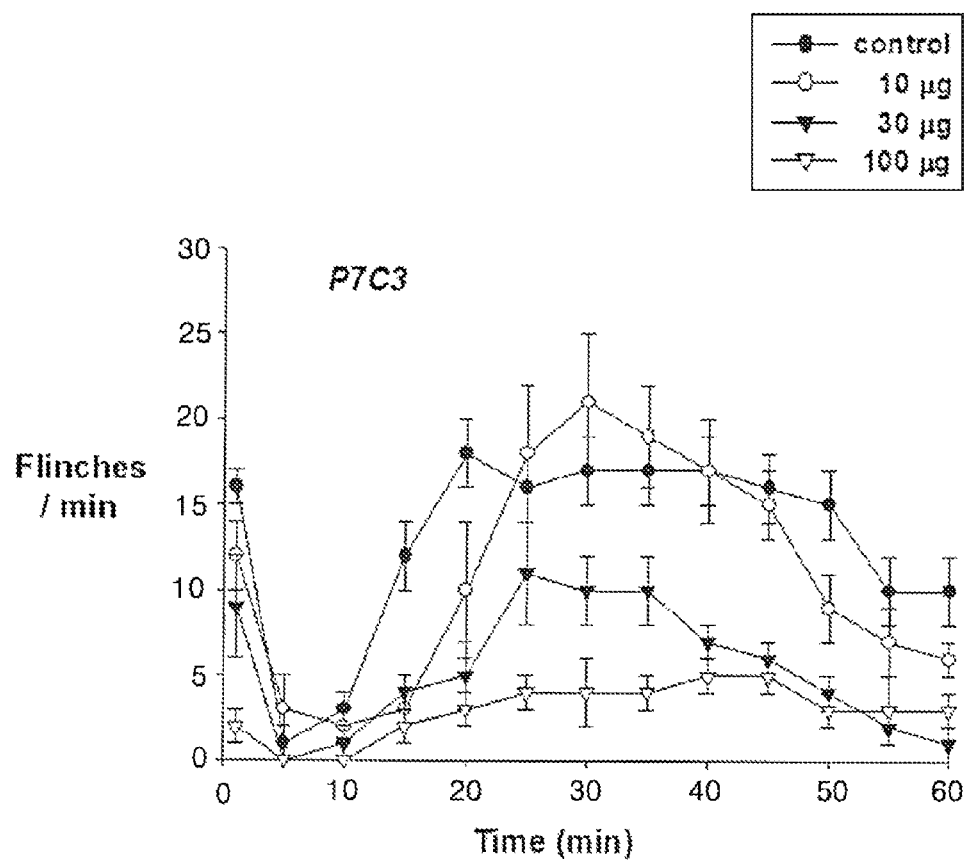
Figure 1B:
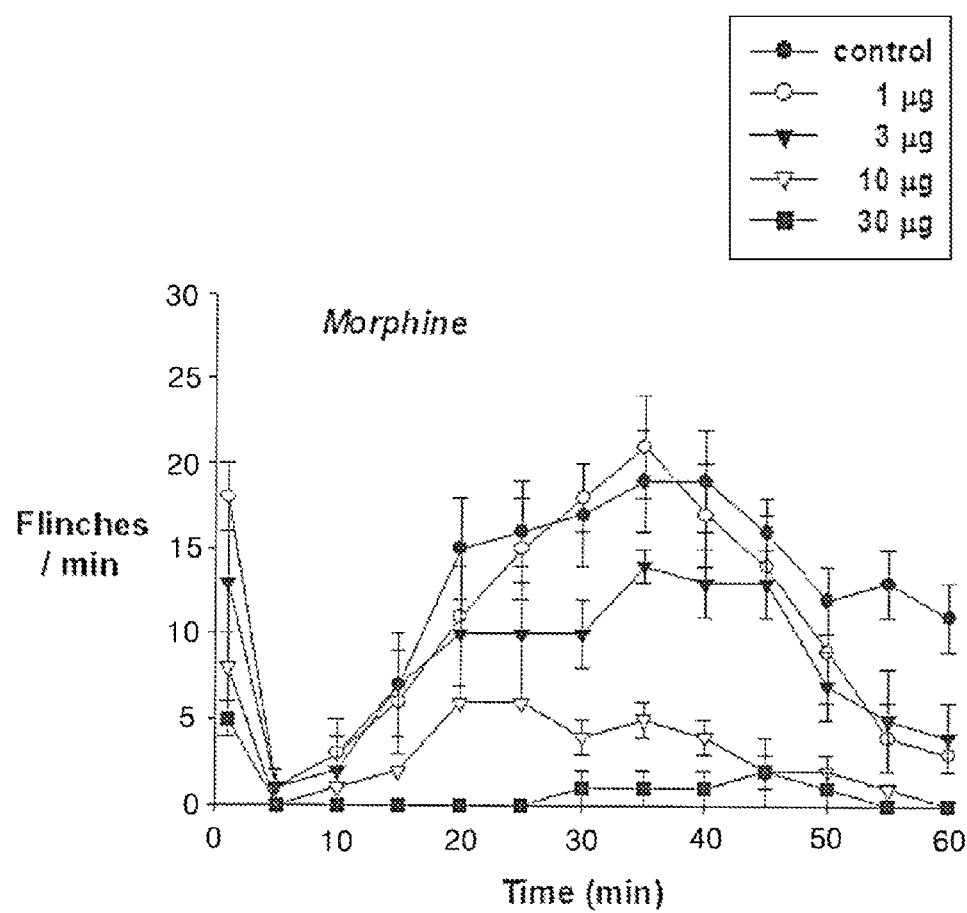
Figure 2A:
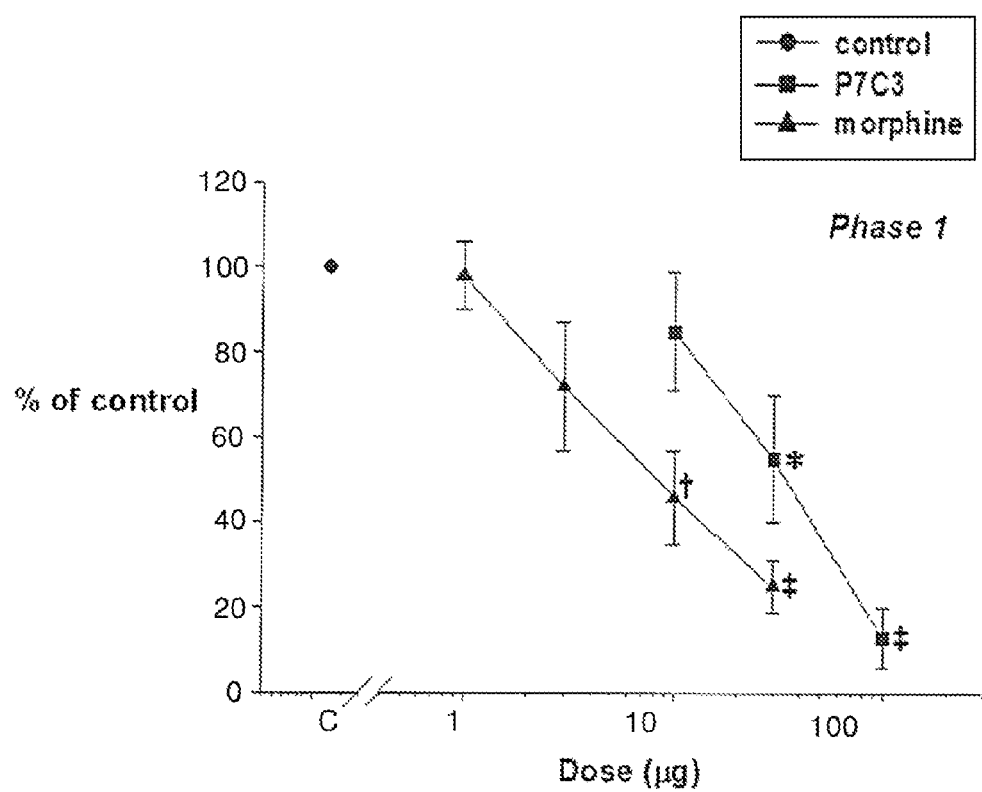
FIGS. 2A and 2B illustrate a dose-response curve of intrathecal P7C3 and morphine as a percentage of a control over flinching in a formalin-induced pain test according to an exemplary embodiment of the present invention.
Figure 2B:
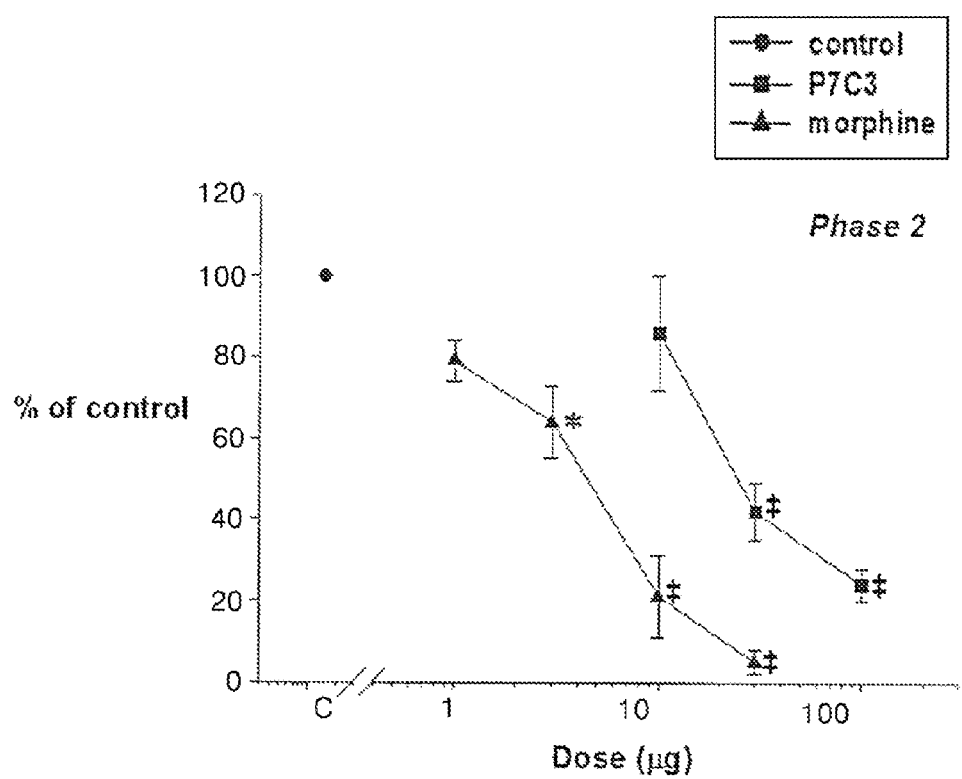

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, exemplary embodiments of the present invention will be described in detail with reference to the accompanying drawings.

The tissue injury-induced pain may be classified into acute pain (Phase 1 pain response) and facilitated pain (Phase 2 pain response), and it is judged that the two pain types occur by mechanisms different from each other. The facilitated pain state is a pain state secondarily generated after a local tissue injury, and means a state in which a pain response is increased even in a continual centripetal stimulation at a very low level.

The present invention relates to an analgesic composition for treating acute and facilitated pain according to these different mechanisms very effectively, and to an analgesic composition which shows surprising synergistic effects by being administered with P7C3 and an opioid analgesic, particularly, morphine.

P7C3, 1-(3,6-dibromo-9H-carbazol-9-yl)-3-(phenylamino)propan-2-ol is a compound having a structure of the following Formula 1, is known to has a neuroprotective effect in brain, has been extensively studied as a drug for treating Parkinson's disease, Lou Gehrig's disease, ADAH, depression, and the like, but has not yet been known about the analgesic effect against pain.

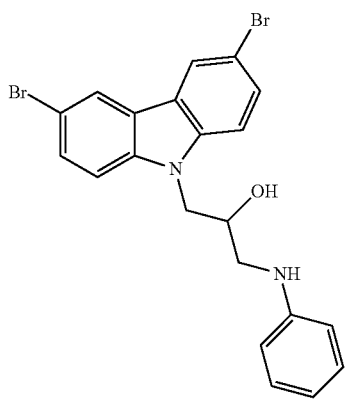

[Formula 1]

As the opioid analgesic, an analgesic selected from mixtures of codeine, hydromorphone, hydrocodone, oxycodone, dihydrocodeine, dihydromorphine, diamorphone, morphine, tramadol, and oxymorphone, or salts thereof may be used. Preferably, morphine or a pharmaceutically acceptable salt thereof may be used.

Morphine, (5α,6α)-7,8-didehydro-4,5-epoxy-17-methyl-morphinan-3,6-diol is a compound having a structure of the following Formula 2, and is a representative opioid analgesic.

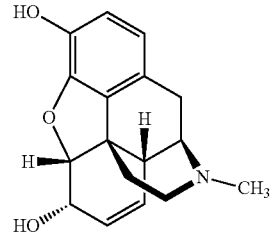

[Formula 2]

The present invention provides a combination of P7C3, pharmaceutically acceptable salts thereof, an opioid analgesic, or pharmaceutically acceptable salts thereof as an analgesic composition for intrathecal administration.

It is preferred that the analgesic composition according to the present invention includes an opioid analgesic and P7C3 in a weight ratio of 8.8:31.8 or 3.9:31. It is preferred for the optimized analgesic effect that a composition including the opioid analgesic and P7C3 in a weight ratio of 8.8:31.8 is administered in the acute pain state, and a composition including the opioid analgesic and P7C3 in a weight ratio of 3.9:31 in the facilitated pain state. The analgesic composition including the opioid analgesic and P7C3 may be administered once, or several times daily, preferably 2 to 4 times.

The appropriate ratio of P7C3 and the opioid analgesic may be determined by standard assay methods which determine the analgesic activity of opioid well known in the art. For example, a phenyl-p-benzoquinone test may be used to measure the analgesic efficacy. A phenyl-p-benzoquinone-induced writhing test for rats and a modified test method thereof (H. Blumberg et al., 1965, Proc. Soc. Exp. Med. 118:763-766) are standard methods which may be used to compare and detect the activity of an analgesic for humans and the activity of another highly relevant analgesic. The data on rats suggested in the isobologram may be applied to other species. The method is composed of a method for reading % $ED_{50}$ administration amount for the ratio of each administration amount in an optimal regression analysis curve from the rat isobologram, a method for multiplying each element by means of an effective administration amount for each species, and a method for forming the administration amount ratio of P7C3 and the opioid analgesic. From the basic correlation for analgesic effects, a range effective for humans may be measured (E. W. Pelikan, 1959, The Pharmacologist 1:73).

The analgesic composition according to the present invention provides a synergistic interaction. Due to the synergistic interaction and/or the addition action by means of a combination of P7C3 and the opioid analgesic, it is possible to reduce the amount of opioid analgesic used. The kind and degree of side effect may be reduced by reducing the amount of opioid analgesic used.

The analgesic composition according to the present invention may further include a vehicle which is generally used in the art for intrathecal administration.

Hereinafter, the present invention will be described with reference to Examples, but the present invention is not limited thereto.

EXAMPLE

Experimental Subject

After permission for all the procedures in the experimental protocol was obtained by The Institutional Animal Care and Use Committee of Chonnam National University, experiments were performed. Adult male Sprague-Dawley rats (250 to 300 g) were used as the experimental subject, four rats per group were housed and kept in a well-controlled vivarium, maintained at 22° C. for 12 hours, with an alternating light/dark cycle and were given food and water ad libitum. Rats were under sevoflurance anesthesia in order to be implanted with an intrathecal catheter, and placed in a stereotaxic apparatus A polyethylene catheter lower end portion was intrathecally inserted so as to be positioned within the lumbar extension portion through an incision in the cisternal membrane. Then, the catheter upper end portion was secured at the skull. After the catheter implantation, rats were again housed in individual cages. After the intrathecal catheter implantation, rats showing movement disorder were excluded in the experiment, and killed by administering an overdose of sevoflurane. Rats showing normal responses were again housed in individual cages in the vivarium, and given a recovery time of 5 days.

Pain Experiment and Experiment Protocol

A formalin experiment was used as a pain evoking experimental tool. 50 μL of a 5% formalin solution was injected subcutaneously into the subcutaneous tissue of a hind paw of the rat. The formalin injection produced abnormal behaviors including a specific behavior (flinching) which lifts up and down the hind paw from the bottom, or behaviors considered as a pain response such as rapid and brief withdrawal of the injected paw. The number of flinches was counted for 1 min periods at 1 and 5 min and at 5 min intervals from 10 to 60 min after the injection. The pain response represented as a flinching response was shown to be biphasic. Therefore, the phase from 0 to 9 minutes after the injection of formalin was defined as Phase 1, and the phase from 10 to 60 minutes was defined as Phase 2. After the behavior study, rats were administered an overdose of sevoflurane, and then killed.

The effect of the experimental drug for the formalin injection was tested for 5 days after the intrathecal catheter implantation. After acclimatization for 15 to 20 min in a restraint cylinder (10×10×30 cm), the rats were allocated to receive one of the experimental drugs, and tested only once. The same volume of the vehicle (saline, 0.1 N NaOH or DMSO) was administered to a control. The total number of rats used in the nociceptive behavioral study was 139 with 6 to 8 rats per group. The investigators were blind as to the administration amount and type of experimental drug used in each rat.

Experimental Example

Evaluation of Response of Intrathecal Administration of P7C3

In order to detect undesirable behaviors induced by P7C3, the highest dose (100 μg) was intrathecally administered to 5 rats of each individual group. Motor function was assessed by the placing-stepping reflex and the righting reflex. The former was evoked by drawing the dorsum of each hind paw across the edge of the table; healthy rats generally try to put the paw ahead into a position for walking. The latter was evaluated by placing the rat horizontally with the rat's back on the table. The healthy rats automatically rise by immediately twisting the body into an upright position. The central nervous system was evaluated through pinna and corneal reflexes. Stimulation was given by using the catheter to touch the ear canal or the cornea. After the stimulation, the healthy rats shake their heads or blink, respectively.

Normality of behavior was judged as present or absent, and each reflex after the intrathecal administration of P7C3 was all normal (present).

Example 1

Effect Experiment of P7C3 and Morphine

Saline, 10, 30, and 100 μg of P7C3 (Tocris Cookson Ltd., Bristol, UK), and 1, 3, 10, and 30 μg of morphine sulfate (Sigma-Aldrich, St. Louis, Mo., USA) were intrathecally administered 10 minutes before formalin injection, and analgesic effects (flinching number analysis) were investigated according to the aforementioned pain experiment. The drug was intrathecally administered by using a manually gear operated syringe pump. All the drugs were administered in an amount of 10 μl, and an additional 10 μl of standard saline was administered in order to wash out the catheter.

The dose ($ED_{50}$), which decreases the formalin response of the control for P7C3 and morphine by 50%, was determined at Phase 1 and the Phase 2, respectively. The $ED_{50}$ of P7C3 and morphine in Phase 1 was 31.8 μg and 8.8 μg, respectively, and the $ED_{50}$ of P7C3 and morphine in Phase 2 was 31 μg and 3.9 μg, respectively.

Example 2

Evaluation of Drug Interaction of Analgesic Composition

In order to analyze the drug interaction of P7C3 and morphine, an iosobolographic analysis was performed.

P7C3 and morphine were simultaneously administered intrathecally in amounts of $ED_{50}$ and ½, ¼, and ⅛ divided doses of $ED_{50}$ of each drug determined in Example 1. The dose was summarized in the following Table 1. And then, $ED_{50}$ of the mixed drug was obtained. The experiment was performed individually in Phase 1 and Phase 2.

TABLE 1

| Dose (μg) | $ED_{50}$ | ½ of $ED_{50}$ | ¼ of $ED_{50}$ | ⅛ of $ED_{50}$ |
|---|---|---|---|---|
| Phase 1 | (31.8 + 8.8) | (31.8 + 8.8)/2 | (31.8 + 8.8)/4 | (31.8 + 8.8)/8 |
| Phase 2 | (31 + 3.9) | (31 + 3.9)/2 | (31 + 3.9)/4 | (31 + 3.9)/8 |

Analysis Method and Result:

Data obtained in Examples 1 and 2 were expressed as means±SEM. The time response data are presented as the number of flinches. The dose-response data are presented as a percentage of the control.

Percentage of the control=(total number of flinches in drug administration group in Phase 1[2]/ number of flinches of control in Phase 1[2])× 100

The analysis results of the data obtained in Example 1 are shown in FIGS. 1A, 1B, 2A and 2B. According to FIGS. 1A and 1B, intrathecal P7C3 and morphine at the highest dose exhibited potential analgesic effects throughout the entire observation period. According to FIGS. 2A and 2B, it was shown that P7C3 and morphine suppressed flinching reactions dose-dependently during Phase 1 and Phase 2 in a formalin experiment. According to these results, it can be confirmed that P7C3 had effects for acute pain and facilitated pain.

Meanwhile, an isobolographic analysis was performed with the data obtained in Example 3. Theoretically, the straight line connecting the $ED_{50}$ of each drug represents additivity of the combined drug. Meanwhile, in order to quantify the degree of interaction, the total fraction value was calculated by using the following Equation.

Total fraction value=($ED_{50}$ of Drug 1 combined with Drug 2/$ED_{50}$ of Drug 1 administered alone)+ ($ED_{50}$ of Drug 2 combined with Drug 1/$ED_{50}$ of Drug 2 administered alone)

Figure 3A:
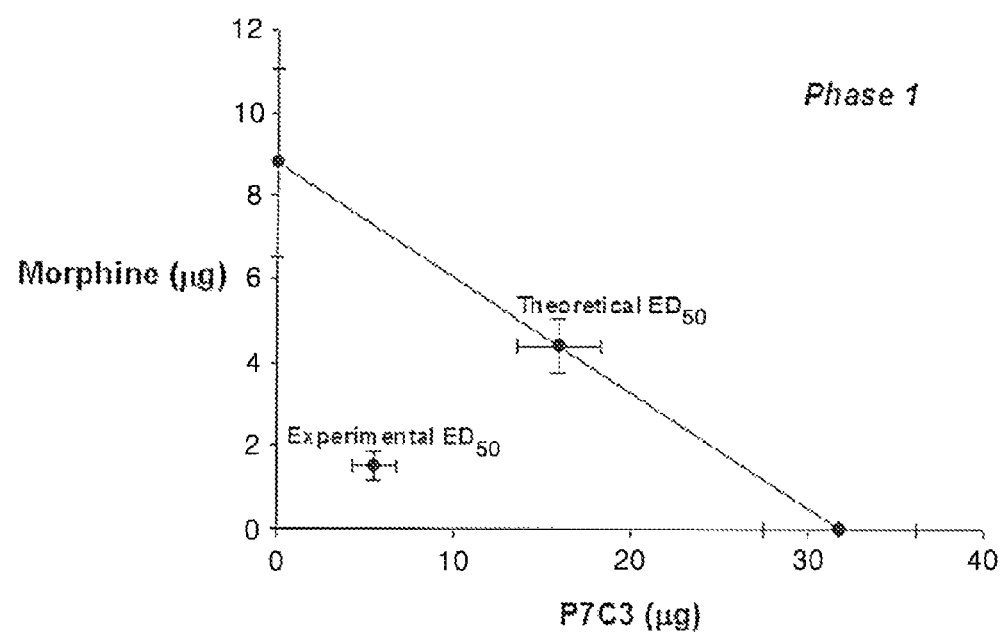
FIGS. 3A and 3B are an isobologram for interaction between intrathecal P7C3 and morphine during the response of Phase 1 (3A) and the response of Phase 2 (3B) in a formalin-induced pain test according to an exemplary embodiment of the present invention. The horizontal and the vertical bars indicate a confidence interval.
Figure 3B:
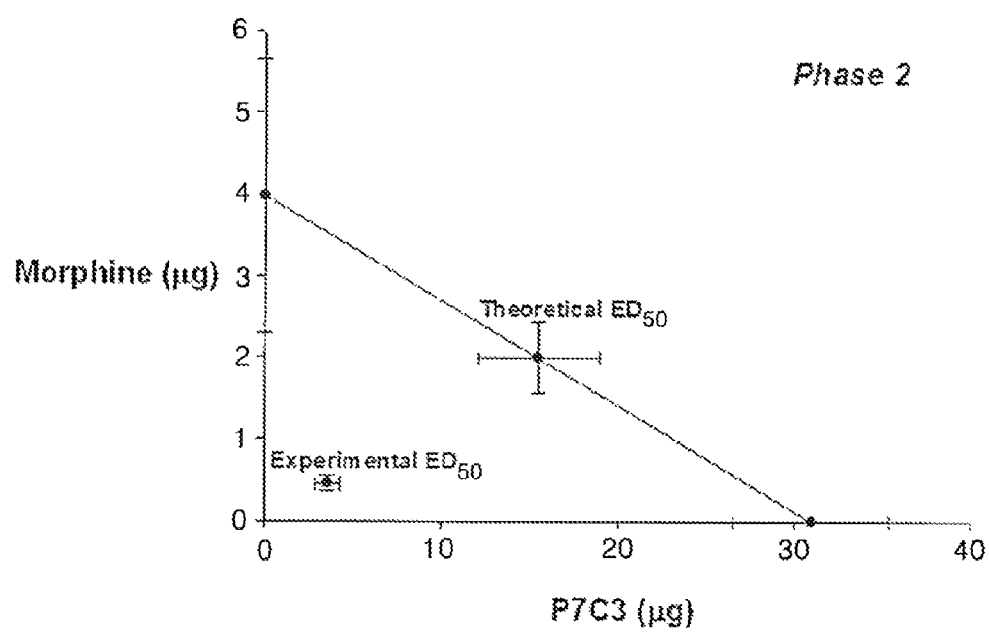

The total fraction value converging to 1 represents an additive interaction, a value exceeding 1 represents an antagonistic interaction, and a value less than 1 represents a synergistic interaction. The analysis results of the data obtained in Example 3 are shown in FIG. 3A, FIG. 3B and the following Table 2.

TABLE 2

| | $ED_{50}$ (95% CI) | |
|---|---|---|
| Preparation | Phase 1 | Phase 2 |
| P7C3 | 31.8 | 31 |
| | (18.9-53.5) | (19.6-48.9) |
| Morphine | 8.8 | 3.9 |
| | (5.2-14.9) | (2.8-5.6) |
| P7C3 + Morphine | 7.0 + 1.9 | 4.0 + 0.5 |
| | (2.7-18.6, 0.7-5.2) | (0.6-26.4, 0.09-3.0) |
| Total fraction value (TFV) | 0.34 | 0.23 |

In the isobologram of the mixture of P7C3 and morphine, the $ED_{50}$ experimentally obtained was present below the theoretical additive line in the two phases. Therefore, the total fraction value for the experimental $ED_{50}$ was less than 1, and was shown to be very significantly lower than that for the theoretical $ED_{50}$. This demonstrates a synergistic interaction between P7C3 and morphine.

Meanwhile, according to FIGS. 3A and 3B, $ED_{50}$ for P7C3 in Phase 1 was similar to $ED_{50}$ in Phase 2 in a formalin experiment. However, $ED_{50}$ of morphine in Phase 1 was two times larger than $ED_{50}$ in Phase 2. This suggests that the intrathecal morphine is more effective for facilitated pain than for acute pain, whereas the validities of the intrathecal P7C3 were similar to each other for acute pain and facilitated pain. When P7C3 was co-administered (combined) with morphine, the ratio of $ED_{50}$ in Phase 1 to $ED_{50}$ in Phase 2 was about 1.8. This suggests that the analgesic effect of P7C3 may be considered to be enhanced more for facilitated pain than for acute pain by combination with morphine.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. An analgesic composition for treating or alleviating tissue injury-induced acute pain and facilitated pain, comprising:
    morphine; and
    a therapeutically effective amount of P7C3 or a pharmaceutically acceptable salt thereof;
    wherein the morphine and P7C3 are included in a weight ratio of 7.0:1.9 or 0.5:4.0, respectively.

2. The analgesic composition of claim 1, wherein the analgesic composition is a formulation administered intrathecally.

* * * * *